US00PP37140P2

(12) United States Plant Patent
Horvath

(10) Patent No.: US PP37,140 P2
(45) Date of Patent: Dec. 9, 2025

(54) ***SCIRPUS PENDULUS* PLANT NAMED 'Stars and Stripes'**

(50) Latin Name: *Scirpus pendulus*
Varietal Denomination: Stars and Stripes

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 18/831,368

(22) Filed: Dec. 17, 2024

(51) Int. Cl.
*A01H 6/00* (2018.01)
*A01H 5/02* (2018.01)

(52) U.S. Cl.
USPC ..... Plt./384

(58) Field of Classification Search
USPC ..... Plt./384
CPC ..... A01H 6/00; A01H 5/02
See application file for complete search history.

*Primary Examiner* — Keith O. Robinson

(57) ABSTRACT

A new, distinct *Scirpus pendulus* plant as illustrated and described characterized by center variegated foliage RHS color 2 D giving the plant a showier foliar display to be unique and stable.

2 Drawing Sheets

Latin name: *Scirpus pendulus*.
Cultivar name: 'Stars and Stripes'.

BACKGROUND OF THE INVENTION

The present invention relates to a new form of *Scirpus pendulus* plant named 'Stars and Stripes'. 'Stars and Stripes' is a naturally occurring sport of an unnamed *Scirpus pendulus*, not patented, characterized by center variegated foliage. The new plant was found in a cultivated area at a wholesale perennial nursery in Leland, IL in 2019. The selection of this plant was due to center variegated foliage giving the plant a showier foliar display. Asexual, vegetative division and tissue culture propagation have been the means of reproduction. Propagation has taken place at a nursery in Hebron, IL since 2020. In 2024 we planted 500 plants in pots. To date these plants have remained uniform in variegation. The new *Scirpus pendulus* has shown to be stable and identical in reproduction to the parent after making over 1000 vegetative divisions from 2020 to 2024. No plants of *Scirpus pendulus* 'Stars and Stripes' have been sold in this country, or anywhere in the world, prior to the filing of this application, nor has any disclosure of the new plant been made prior to the filing of this application with the exception of that which was disclosed within one year of the filing of this application and was either derived directly or indirectly from the inventor. Actual first date of sale was May 6, 2024.

SUMMARY OF THE INVENTION

In the following description, color references are made to The Royal Horticultural Society Colour Chart (2001). The following traits have been repeatedly observed and represent the characteristics of the new cultivar. The new *Scirpus pendulus* has not been observed under all possible environmental conditions. These attributes in combination distinguish 'Stars and Stripes' from all other selections of *Scirpus pendulus* known to the Inventor. The new *Scirpus pendulus* plant named 'Stars and Stripes' has shown the variegated foliage giving the plant a showier foliar display to be unique and stable.

Plants of the new *Scirpus pendulus* can be compared to plants of *Scirpus pendulus* the species, not patented. The new *Scirpus pendulus* has variegated foliage compared to the species which has all green foliage. More specifically the leaves of the new *Scirpus pendulus* plant named 'Stars and Stripes' have yellow centers and green edges to the foliage.

For the sake of comparison to other related known *Scirpus pendulus* varieties, there are none that the breeder knows of.

DESCRIPTION OF PHOTOGRAPHS

The accompanying colored photographs illustrate the overall appearance and distinct characteristics of two year-old plants as grown in a container outdoors in Hebron, IL, USA.

Figure 1:
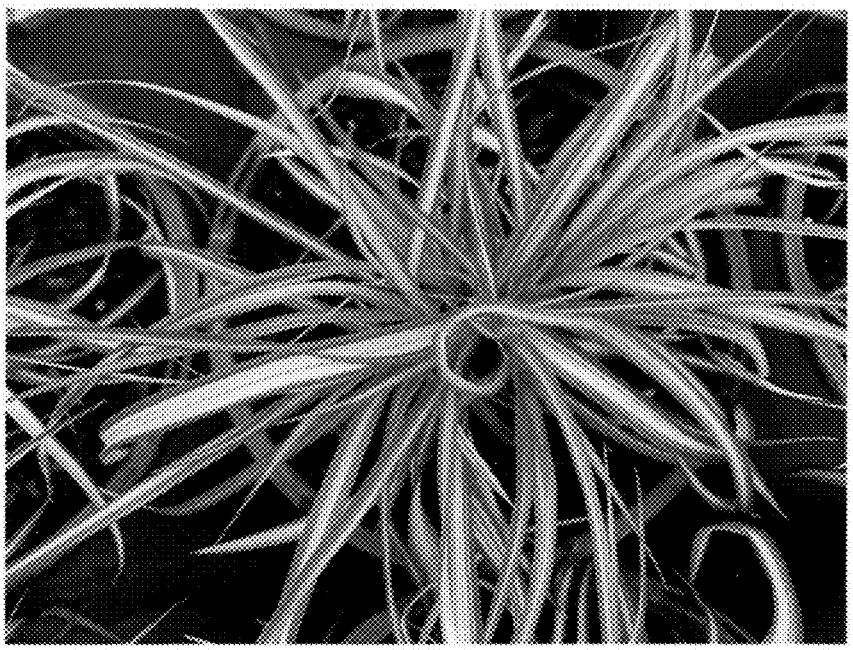

FIG. 1. Shows a plant foliage in April on a 2 year old plant.

Figure 2:
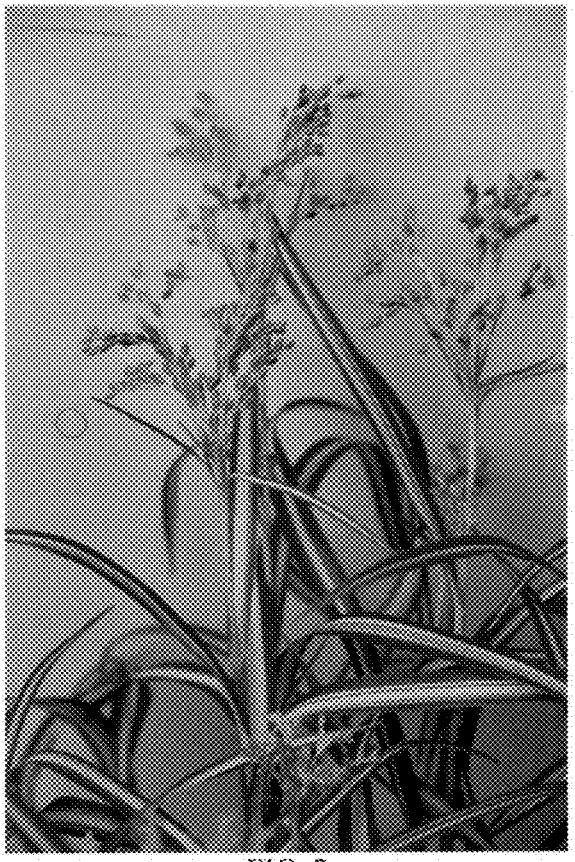

FIG. 2. Shows the appearance in bud in May on a 2 year old plant.

Figure 3:
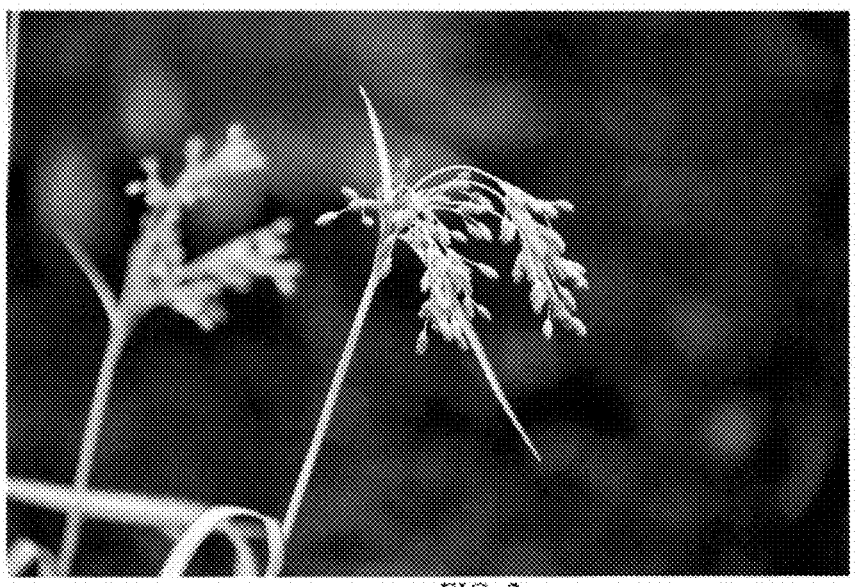

FIG. 3. Shows a close up of the inflorescence in July on a 2 year old plant.

DETAILED BOTANICAL DESCRIPTION

In the following description, color references are made to The Royal Horticultural Society Colour Chart (2001). The plant herein described is a two year old plant grown in full sun and irrigated in Hebron, IL US.

Botanical classification: *Scirpus pendulus* plant named 'Stars and Stripes'.
Parentage: Unnamed *Scirpus pendulus*.
Propagation: Vegetative division.
Culture: Grows best in part shade in well drained to dry soil.
Growth rate: Moderate.
Plant type: Deciduous perennial grass, growing in culms.
Plant description: Overall habit of the new *Scirpus pendulus* is tufted basal mounds that are stoloniferous with arching flower stems beginning in June. Vigor is moderate.
*Plant height.*—60 cm.
*Plant width.*—53 cm.

*Flower stem*.—Triangular, diameter 3 mm. length: 53 cm.

Foliage:

*Sheath color*.—Similar to the species with color of 141 A on the edge of the foliage with some stripes of variegated green and yellow foliage 139 B, 137 C and 2 D in the center. These colors start in spring and remain the same into fall.

*Sheath size*.—4 cm long and 4 mm wide.

*Shape*.—Linear, arching blade.

*Petiole*.—None.

*Apex*.—Attenuate.

*Aspect*.—Upright, then arching down to the ground.

*Leaf venation*.—Parallel, 80 to 50 percent have 141 A, 139 B, 137 C on the edge of the leaf with 30 to 50 percent of 2 D color in the center of the leaf. The color matches leaf color.

*Margins*.—Entire.

*Leaf persistence*.—Deciduous with some foliage remaining over winter.

*Leaf size*.—Length 20 cm, width 1 mm.

*Leaf number*.—7 per culm, 112 per plant.

*Leaf arrangement*.—Equitant, 6-8 cm between leaves, emerging from the center, sheathed to the base.

*Leaf durability to stress*.—Moderate.

*Adaxial leaf description*.—Surface — glabrous, smooth, color — upon emerging and mature the leaf edge is 141 A, 139 B, 137 C and the leaf center is 2 D.

*Abaxial leaf description*.—Surface — glabrous, smooth, color — upon emerging and mature the leaf edge is 141 A, 139 B, 137 C, 139 B and the leaf center is 3 D.

Floret description:

*Inflorescence type*.—Terminal spikelets, with smaller spikelets below arising from the uppermost leaf axil. Separated by 4 cm. Overall size of a mature inflorescence — 10 cm wide and 8 cm long.

*Floret bud*.—Ovate, 5 mm wide, 4 cm long.

*Floret scale size and shape*.—Similar to the species 1 mm wide and 2 mm long, lance-elliptic to cylindrical, margin entire, apex acute, surface smooth, and dull in appearance.

*Floret scale color*.—Emerging 152 A and 152 B, mature 199A.

*Spikelet aspect*.—Nodding.

*Spikelet shape and persistence*.—Oblongoid-ellipsoid, persistent.

*Pedicels*.—4-5 cm long and less than 1 mm wide.

*Inflorescence stem color*.—151 C.

*Inflorescence color*.—Upon opening the color is 152 A and 152 B and maturing to 199 A.

*Flower number*.—Approximately 4 florets per spikelet, perfect.

*Individual spikelets size*.—Overall 5 mm wide, 10 mm long.

*Spikelet color*.—152 A and 152 B.

*Stamens*.—3 in number, held terminally, less than 1 mm wide, 2 mm long, color N144 C.

*Style*.—Tripartite, 3 held laterally, less than 1 mm wide, 2 mm long, N144 C, surface smooth, and dull in appearance.

*Rachis*.—6 mm long 1 mm in diameter, held upright, color N144 C.

*Lastingness of the inflorescence*.—Flower last around 14 days.

*Fertility*.—Fertile.

*Bloom period and duration*.—Early June through the end of June.

*Scent*.—No scent noticed.

*Root description*.—Short stolons with dense fibrous roots, color 159 D, less than 1 mm wide, moderately branched.

*Fruit*.—Achene, appears identical to the species *Scirpus pendulus* which are three angled, ovoid in shape, 1 mm long, 1 mm wide. Each achene is surrounded by 5-6 bristles, 2 mm in length and 1 mm in width, color is 177 B. Scales are 2 mm in length, and 1 mm in width, color is 177 B.

*Hardiness*.—USDA Zones 4-9.

*Diseases and pests resistance*.—Plants are not susceptible to any major pests or diseases.

*Culture*.—Grows best in full sun in moist soils.

I claim:

1. A new, distinct *Scirpus pendulus* plant named 'Stars and Stripes' plant as illustrated and described herein.

* * * * *